United States Patent [19]
Haaga

[11] Patent Number: 5,487,392
[45] Date of Patent: Jan. 30, 1996

[54] BIOPXY SYSTEM WITH HEMOSTATIC INSERT

[76] Inventor: John R. Haaga, 4309 N. Hilltop, Chagrin Falls, Ohio 44022

[21] Appl. No.: 151,914

[22] Filed: Nov. 15, 1993

[51] Int. Cl.$^6$ .................................................. A61B 10/00
[52] U.S. Cl. ............................................ 123/753; 128/751
[58] Field of Search .................................. 128/751, 752, 128/753, 754, 755, DIG. 8; 604/8, 265

[56] References Cited

U.S. PATENT DOCUMENTS

| | | | |
|---|---|---|---|
| 2,198,319 | 4/1940 | Silverman | 128/754 |
| 3,106,483 | 10/1963 | Kline et al. | 604/8 X |
| 3,358,684 | 12/1967 | Marshall . | |
| 4,412,947 | 11/1983 | Cioca | 128/DIG. 8 X |
| 4,626,286 | 12/1986 | Lubbs | 128/DIG. 8 X |
| 4,708,147 | 11/1987 | Haaga | 128/753 |
| 4,749,689 | 6/1988 | Miyata et al. | 128/DIG. 8 X |
| 4,785,826 | 11/1988 | Ward | 128/759 |
| 4,827,940 | 5/1989 | Mayer | 128/642 |
| 4,838,280 | 6/1989 | Haaga | 128/751 |
| 4,902,290 | 2/1990 | Fleckenstein et al. | 128/DIG. 8 X |
| 4,936,835 | 6/1990 | Haaga | 604/265 |
| 5,061,281 | 10/1991 | Mares et al. | 623/11 |
| 5,080,655 | 1/1992 | Haaga | 604/265 |
| 5,195,988 | 3/1993 | Haaga | 604/265 |
| 5,231,212 | 1/1994 | Savage et al. | 604/265 |
| 5,326,350 | 7/1994 | Li | 128/DIG. 8 X |

*Primary Examiner*—Sam Rimell
*Attorney, Agent, or Firm*—Vickers, Daniels & Young

[57] ABSTRACT

A biopsy needle has coaxial, telescopically interengaged stylet, inner and outer cannulas which are axially and rotatably displaceable relative to one another. The stylet has a distal portion provided with a cutting recess for severing a biopsy specimen from a site in a patient, and the inner cannula has a distal portion for cutting and capturing the specimen in the recess for removal from the site upon withdrawal of the needle from the patient. The distal portion of the inner cannula is partially cut away to provide an insert recess which supports a semi-circular insert of hemostatic collagen which remains at the site upon removal of the needle to minimize hemorrhagic complications by promoting blood clotting. The insert and the distal portion of the inner cannula have radially outer surfaces of corresponding radius whereby the distal portion of the inner cannula and the insert supported thereon are received within the distal end of the outer cannula prior to use of the needle.

31 Claims, 3 Drawing Sheets

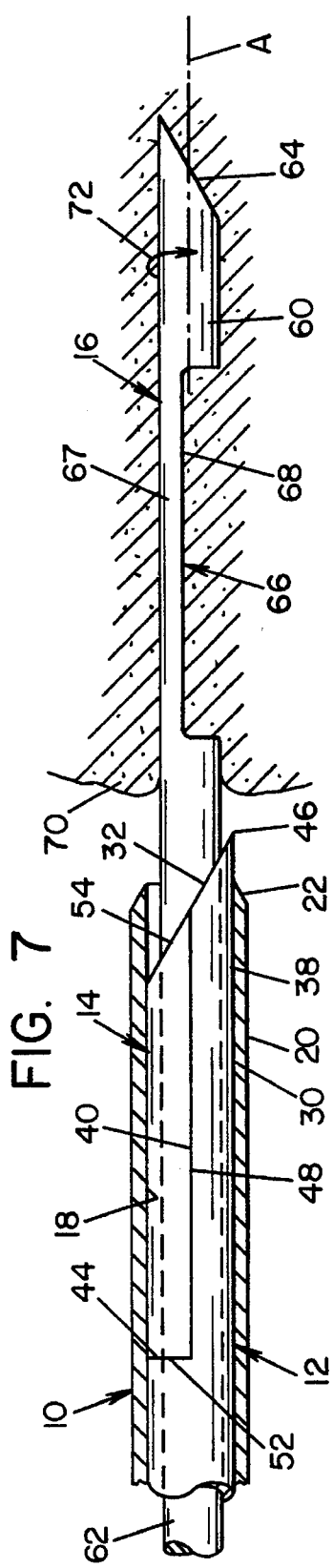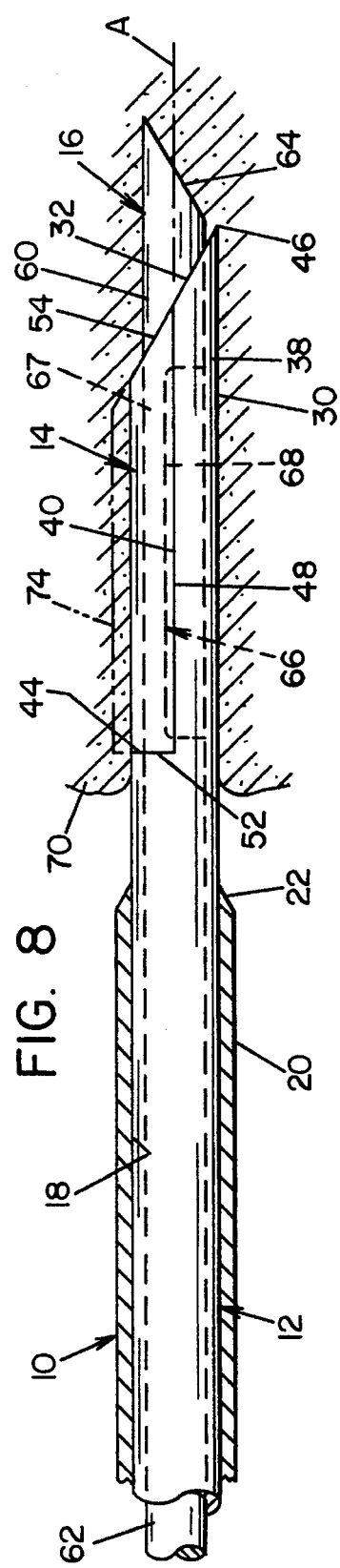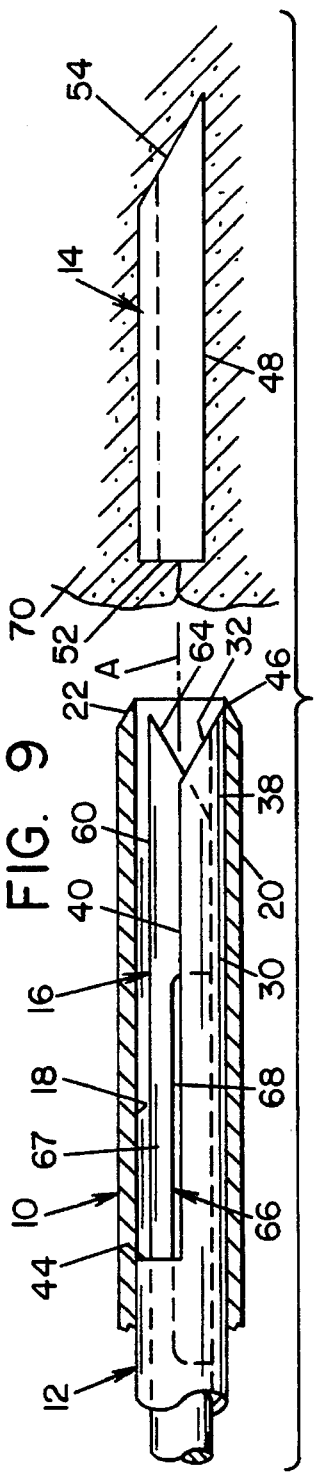

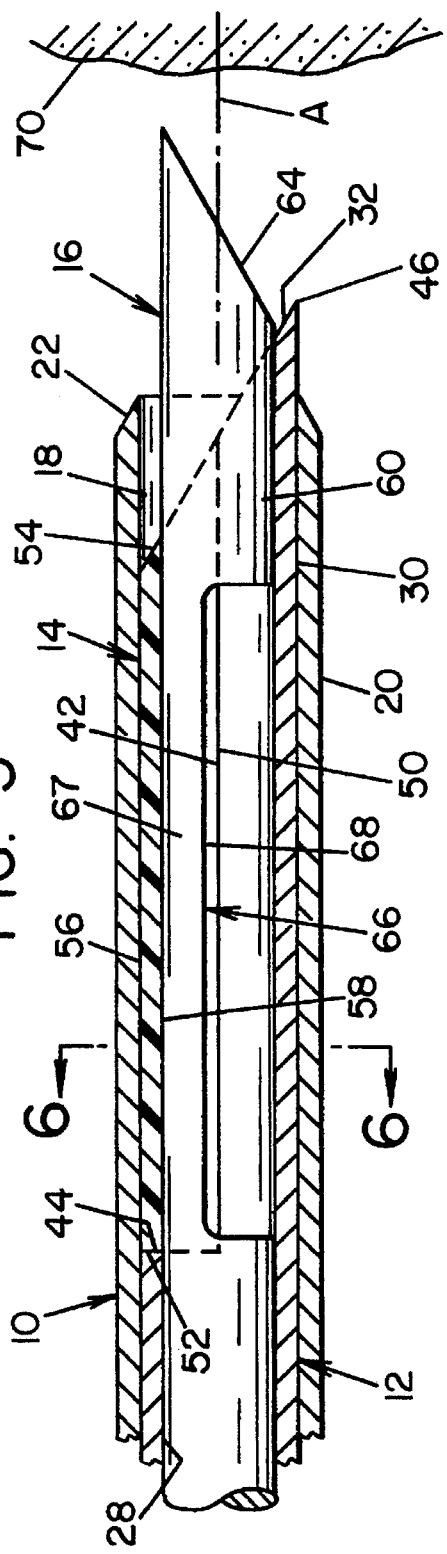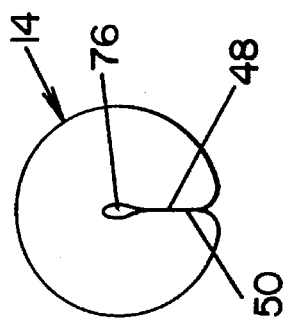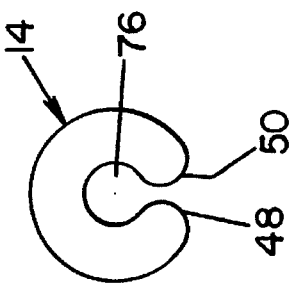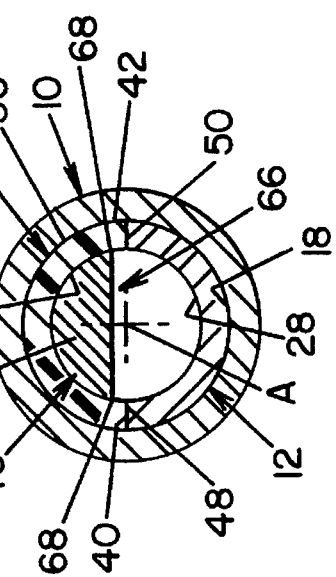

BIOPXY SYSTEM WITH HEMOSTATIC INSERT

BACKGROUND OF THE INVENTION

This invention relates in general to surgical needles and, more particularly, to improvements in a biopsy needle construction which minimizes hemorrhagic complications upon removal of the needle from a site in a patient.

The invention is particularly applicable to the removal of tissue and like specimens from the human body and will be described in particular with reference thereto. It will be appreciated by those skilled in the art, however, that the invention has broader application and may be used for selective extraction of tissue samples and the like from other living matter such as animals.

A biopsy needle of the character to which the present invention relates is a side cut needle such as the type commercially known as "Trucut" needles. Such a side cut needle includes a solid stylet telescopically received within an inner tubular cannula which in turn is telescopically received within an outer tubular cannula by which the stylet and inner tubular cannula are supported for axial and rotative displacement relative to one another and to the outer cannula. The side cut needle is inserted into a patient until the distal end of the outer cannula reaches the lesion where the biopsy specimen is to be taken. The stylet is then advanced relative to the outer and inner cannulas into the lesion to the biopsy site. The stylet is provided with a cutting recess in the distal portion thereof and, when the stylet reaches the biopsy site, the stylet is rotated so that a cutting edge of the cutting recess severs the tissue. The inner cannula is then advanced relative to the outer cannula and over the stylet to cut the tissue into the cutting recess and to cover the recess and thus entrap the specimen within the recess for removal from the site by retracting the stylet and inner cannula into the outer cannula and then withdrawing the needle from the patient.

In a number of my prior U.S. Pat. Nos. 4,708,147; 4,838,280; 4,936,835; 5,080,655; and 5,195,988, and in my co-pending patent application Ser. No. 896,588 filed Jun. 10, 1992 entitled "Sheath For Wound Closure Caused By A Medical Tubular Device", the disclosure of all of which patents and co-pending application are incorporated herein by reference, there is disclosed a side cut needle of the foregoing character in which the equivalent of the inner cannula referred to above is provided with a tubular sheath of a absorbable gelatin material or a non-bioabsorbable hemostatic collagen for minimizing bleeding of the patient from the biopsy site upon removal of the needle. In this respect, the hemostatic sheath is applied about the distal portion of the inner cannula and is advanced therewith into the lesion for the inner cannula to cover the cutting recess in the stylet which, as described above, is initially inserted into the lesion and rotated to sever a biopsy specimen to be removed from the lesion. In accordance with my earlier arrangements, the equivalent of the outer cannula referred to hereinabove is also inserted into the lesion and has a distal end adjacent the axially inner end of the hemostatic sheath for positioning the sheath in the location where the biopsy specimen was taken when the specimen is withdrawn therefrom. More particularly in this respect, when the biopsy specimen is cut and enclosed in the cutting recess as described above, the stylet and inner cannula are withdrawn or retracted relative to the outer cannula which is held stationary at the site, whereby the axially inner end of the sheath engages the outer cannula and is held in its position within the lesion as the inner cannula and stylet are retracted into the outer cannula. When the sheath is released from the inner cannula, the needle is withdrawn from the site of the lesion.

While the hemostatic sheath in my earlier arrangements serves its intended purpose to minimize bleeding from the biopsy site by compressing the bleeding tissue surrounding the biopsy site and by swelling upon absorbing body fluid so as to increase the compressive effect, there are a number of disadvantages with respect to the structure and manipulation of the component parts of the biopsy needle in connection with obtaining a biopsy specimen. More particularly in this respect, by providing the hemostatic sheath in the form of a sleeve surrounding the inner cannula and which sleeve has an outer diameter generally corresponding to that of the outer cannula in a standard side cut biopsy needle, the diameter of the needle portion which must penetrate the lesion is greater than that required with a standard side cut needle wherein only the stylet and inner cannula need penetrate the lesion in order to obtain a biopsy specimen therefrom. Thus, the size of the puncture as the needle penetrates the lesion is larger than with a standard side cut needle, whereby the possibility of severing blood vessels while positioning the needle and severing the biopsy specimen is increased as is the resultant bleeding caused thereby.

In addition to the above, the standard side cut needle has to be modified to include an outer cannula which axially accommodates the hemostatic sleeve on the outer periphery of the inner cannula and which operates to push the sleeve off of the latter at the biopsy site following severing and covering of the biopsy specimen. Accordingly, automated operation of the needle through the use of a conventional "gun" which will actuate the standard Trucut needle to advance and rotate the stylet, advance the inner cannula to cover the specimen cutting recess in the stylet, and retract the stylet and inner cannula relative to the outer cannula is not possible. Therefore, the component parts of the needle must be manually manipulated to retrieve a biopsy specimen. Moreover, the manual manipulation of the component parts of the needle is much more complex than that required to manually retrieve a biopsy specimen using a standard side cut needle. In this respect, after the stylet has been extended into the biopsy site and rotated to severe the specimen, both the inner cannula with the hemostatic sheath thereon and the outer cannula axially behind the sheath must be advanced into the biopsy site so as to cover the specimen cutting recess in the stylet and position the outer cannula to engage and hold the hemostatic sheath at the biopsy site during retraction of the inner cannula and stylet therefrom. Still further, the latter requires holding the outer cannula in place and simultaneously withdrawing the inner cannula and stylet thereinto so as to displace the hemostatic sheath from the inner cannula. Such manual manipulations of the component parts of the needle are more time consuming than desirable and increase the possibility of movements being imparted to the needle during such manipulation which in turn increase the possibility of hemorrhagic complications.

Yet a further disadvantage of my earlier biopsy needle resides in the fact that the hemostatic sheath in being disposed about the inner cannula and forwardly of the distal end of the outer cannula is exposed to infectious microorganisms prior to use and to body fluids from the time of initial penetration of the patient's body until such time as the sheath is positioned at the biopsy site and displaced from the inner cannula. If the material of the sheath is a gelatin material or a hemostatic collagen, the material of the sheath begins to absorb body fluids immediately upon exposure thereto and to swell. It will be appreciated, therefore, that by the time the stylet has been advanced into the lesion and rotated to sever the biopsy specimen, the outer diameter of the sleeve may have increased considerably whereby advancement of the inner cannula into the biopsy site with the hemostatic sheath thereabout enlarges the puncture an thus the possibility of rupturing blood vessels even beyond that resulting from the larger initial diameter of the hemostatic sheath relative to that of the inner cannula in a standard needle construction.

SUMMARY OF THE INVENTION

In accordance with the present invention, an improved side cutting biopsy needle is provided by which the foregoing disadvantages are minimized or overcome while, at the same time, maintaining the advantage of depositing a hemostatic insert in the biopsy site upon removal of the needle therefrom. More particularly in accordance with the invention, the distal portion of the inner cannula is provided with a recess which supports a hemostatic insert for displacement therewith into the biopsy site in conjunction with advancing the inner cannula over the cutting recess in the stylet of the needle following rotation thereof to sever a specimen at the site. The stylet and inner cannula have corresponding extended and retracted positions relative to the outer cannula and, in the retracted positions prior to use, the distal portions of the stylet and inner cannula, and the insert carried by the latter, are within the distal portion of the outer cannula. Accordingly, when the needle is inserted in a patient's body to move the distal end of the distal portion of the outer cannula to a position adjacent the lesion, and the stylet is then extended relative to the outer cannula to penetrate the lesion and is rotated to sever a biopsy specimen therefrom, the inner cannula and the hemostatic insert supported thereon remain within the distal portion of the outer cannula. Thus, the hemostatic insert is advantageously protected from exposure to infectious micro-organisms prior to use and during use is protected from exposure to body fluids by the outer cannula during the needle inserting and specimen severing stages. When the inner cannula is advanced into the biopsy site, the distal portion thereof adjacent the hemostatic insert support recess spans the specimen cutting recess in the stylet. The insert is simultaneously pushed into the site by a portion of the recess in which it is supported. The stylet and inner cannula are then displaced into their retracted positions relative to the outer cannula to remove the specimen from the site, and the needle is withdrawn from the patient. The hemostatic insert merely rests in the inner cannula recess and is freely slidable axially outwardly of the distal end thereof whereby, upon withdrawal of the inner cannula from the site, the insert remains in the biopsy site.

It will be appreciated that the inner cannula and hemostatic insert arrangement according to the present invention minimizes the diametrical dimension of the puncture in the lesion by the needle to that of the inner cannula in a standard side cut needle, thus to minimize the possibility of hemorrhagic complications. It will be further appreciated that the hemostatic insert in simply resting on the inner cannula for sliding displacement therefrom enables the insert to remain at the biopsy site without the need for a pushing component to assure that the insert remains at the site and without the need for a special manipulating of the component parts of the needle to remove the insert therefrom. The latter advantageously enables automated operation of the side cut needle through the use of well known "guns" for operating the latter.

The hemostatic insert can be of a bioabsorbable, non-bioabsorbable or semi-bioabsorbable material such as, for example, collagen, gelatin, .cellulose, absorbable polymers and combinations thereof. Preferably, the insert is non-bioabsorbable collagen which is preferred because of its faster and greater swelling upon exposure to body fluids. In a preferred embodiment, the insert is semi-circular in cross-section and, upon exposure to body fluids, expands radially and circumferentially into a somewhat circular, solid plug configuration. The insert can also be of a bioabsorbable material such as gelatin which, as is well known, initially expands at the biopsy site to occlude the flow of blood therefrom and, subsequently, dissolves within the body. In either event, or in connection with the use of other material to form the hemostatic insert, the insert can be coated or otherwise provided with thrombin which, again as is well known, is a protein which promotes blood clotting.

It is accordingly an outstanding object of the present invention to provide an improved biopsy needle of the side cut type having the capability of depositing a hemostatic insert in a biopsy site in conjunction with the taking of a biopsy specimen therefrom.

Another object is the provision of a biopsy needle of the foregoing character wherein the hemostatic insert is carried on the distal end of the inner cannula of the needle and, prior to use and prior to insertion of the inner cannula into the biopsy site, is disposed in the distal portion of the outer cannula and thus protected from exposure to infectious micro-organisms and exposure to body fluids.

A further object is the provision of a biopsy needle of the foregoing character wherein the hemostatic insert rests in a recess provided therefore in the distal portion of the inner cannula in a manner which provides for the insert to be pushed into the biopsy site by the inner cannula and to be freely slidable axially outwardly thereof, whereby the insert remains in the biopsy site upon removal of the inner cannula and stylet of the needle therefrom.

Yet another object is the provision of a biopsy needle of the foregoing character in which the stylet, inner, and outer cannula components of the needle are structured and structurally interrelated in a manner which accommodates automated operation of the needle by a gun for the latter purpose as well as manual operation by providing the proximal portions of the needle components with handle elements by which the needle components can be manually manipulated.

A further object is the provision of a biopsy needle of the foregoing character which enables placement of a hemostatic insert within the biopsy site with less resistance and with fewer and simpler manipulations of the component parts of the needle than heretofore required.

Still a further object is the provision of biopsy needle of the foregoing character wherein the hemostatic insert is arcuate in cross-sectional configuration and constructed of collagen, whereby the insert when deposited in the biopsy site absorbs body fluids so as to swell and distend into a generally circular plug which remains in the biopsy site.

BRIEF DESCRIPTION OF THE DRAWING

The foregoing objects, and others, will in part be obvious and in part pointed out more fully hereinafter in conjunction with the written description of a preferred embodiment of the invention illustrated in the accompanying drawings in which:

FIG. 5 is a sectional side elevation view showing the distal portions of the outer and inner cannulas, the hemostatic insert, and the distal portion of the stylet in assembled relationship prior to use of the needle;

FIG. 6 is a cross-sectional view of the needle taken along line 6—6 in FIG. 5;

FIGS. 7–9 are side elevation views, partially in section, showing the various positions of the component parts of the needle as a biopsy specimen is taken; and FIGS. 10 and 11 are cross-sectional elevation views schematically illustrating the swelling of the hemostatic insert in the biopsy site following removal of the needle therefrom.

DESCRIPTION OF THE PREFERRED EMBODIMENT

Figure 1:
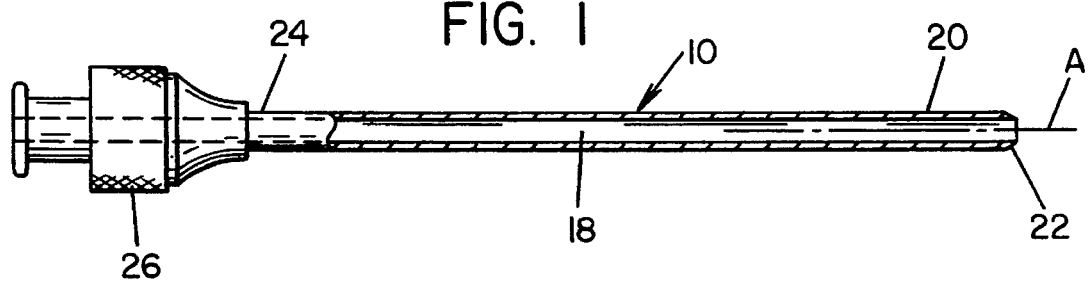
FIG. 1 is a sectional side elevation view of the outer cannula of a biopsy needle in accordance with the invention.
Figure 2:
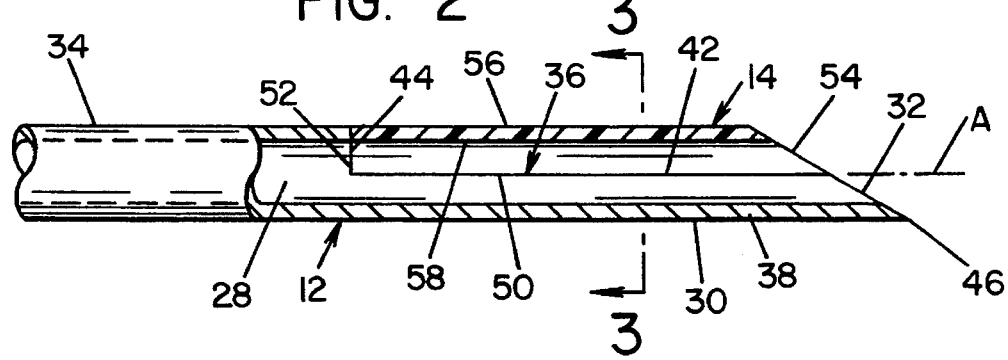
FIG. 2 is a sectional side elevation view of the inner cannula of the needle and the hemostatic insert supported on the distal portion thereof.
Figure 3:
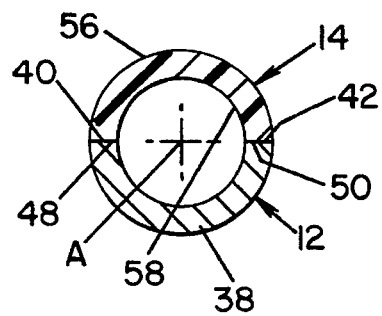
FIG. 3 is a cross-sectional view of the inner cannula and insert looking in the direction of line 3—3 in FIG. 2.
Figure 4:
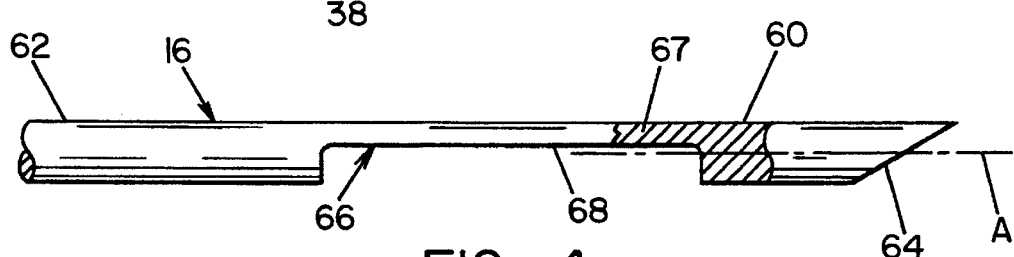
FIG. 4 is a sectional side elevation view of the stylet of the needle.

Referring now in greater detail to the drawings, wherein the showings are for the purpose of illustrating a preferred embodiment of the invention only, and not for the purpose of limiting the invention, FIGS. 1–4 of the drawing illustrate the individual component parts of a needle in accordance with the present invention, and FIGS. 5 and 6 illustrate the component parts in assembled relationship prior to use of the needle. More particularly, the needle includes an outer tubular cannula 10 as shown in FIG. 1, an inner tubular cannula 12 as shown in FIG. 2 and which carries a hemostatic insert 14 as described more fully hereinafter, and a solid circular stylet 16 as shown in FIG. 4. Outer cannula 10 is circular in cross-section, has an axis A and a circular passageway 18 therethrough. The outer and inner cannulas and the stylet are coaxial when assembled and, accordingly, these components are illustrated in the drawings and described hereinafter as having a common axis A. Outer cannula 10 further includes a distal portion 20 having a distal end 22, which is preferably tapered, and a proximal portion 24 which extends from distal portion 20 and includes a handle 26 by which the needle is held during use.

Tubular inner cannula 12 is circular in cross-section and has an outer diameter which provides for the inner cannula to be received in passageway 18 of outer cannula 10 and supported therein for axially sliding and rotative displacement relative thereto. Inner cannula 12 has a circular passageway 28 therethrough and includes a distal portion 30 having a distal end 32 and a proximal portion 34 extending axially inwardly from distal portion 30. While not shown, it will be appreciated that proximal portion 34 includes a handle by which the inner cannula is adapted to be manually displaced relative to outer cannula 10. In the orientation illustrated in the drawings, the upper portion of distal portion 30 of inner cannula 12 is radially and axially cut away to provide a hemostatic insert supporting recess 36 and an arcuate wall 38 having circumferentially spaced apart, axially extending side edges 40 and 42. Side edges 40 and 42 have axially outer and inner ends, not designated numerically, and recess 36 has a circumferentially extending axially inner end edge 44 between the axially inner ends of side edges 40 and 42. Recess 36 includes axially extending insert recess edges which are provided by side edges 40 and 42. Distal end 32 of distal portion 30 of inner cannula 12 is provided by beveling the axially outer end of arcuate wall 38, which beveling provides a cutting tip 46 at the distal end of the inner cannula. Preferably, axially extending side edges 40 and 42 of recess 36 and arcuate wall 38 lie in a diametrical plane through axis A, whereby the arcuate wall is semi-circular in cross-section.

Hemostatic insert 14 is preferably formed of collagen and, in the embodiment illustrated, is semi-circular in cross-section and has circumferentially spaced apart axially extending side edges 48 and 50 respectively resting on side edges 40 and 42 of recess 36. Insert 14 further includes a circumferentially extending inner edge 52 which engages against axially inner end edge 44 of recess 36, and a circumferentially extending axially outer end edge 54. While the latter edge is shown as being beveled so as to be coplanar with the edge of distal end 32 of distal portion 30, the insert could have an axially outer end transverse to axis A. Insert 14 has a radially outer surface 56 preferably having a radius of curvature corresponding to that of the outer surface of arcuate wall 38. In any event, surface 56 id dimensioned relative to axis A so as to provide for the insert when on the distal portion of the inner cannula to be received in distal portion 20 of outer cannula 10 when the component parts of the needle are in the assembled positions thereof prior to use of the needle, as shown in FIG. 5 of the drawing. Similarly, and as will become more apparent hereinafter, insert 14 has a radially inner surface 58 dimensionally interrelated with axis A and stylet 16 so as to allow the stylet to slide relative thereto during displacement of the stylet relative to the inner cannula.

Stylet 16 is solid and circular in cross-section having a diameter which provides for the stylet to be received in passageway 28 of inner cannula 12 and supported therein for axial and rotative displacement relative thereto. Stylet 16 includes a distal portion 60 and a proximal portion 62 extending axially inwardly therefrom. While not illustrated, it will be appreciated that proximal portion 62 of stylet 16 is provided with a handle to facilitate manual manipulation of the stylet relative to the outer and inner cannulas. The axially outer end of distal portion 60 of stylet 16 is beveled to provide a distal tip or end 64, and the distal portion is radially and axially cut away at a location spaced axially inwardly from distal end 64 to provide a specimen cutting recess 66 and a solid portion 67 of the stylet spanning the recess. Recess 66 includes axially extending cutting edges 68 for severing a specimen at the biopsy site during use of the needle.

When assembled, inner cannula 12 and stylet 16 are displaceable between retracted and extended positions relative to outer cannula 10 and, prior to use, are in the retracted positions thereof shown in FIG. 5 and in which distal portions 30 and 60 of the inner cannula and stylet, respectively, and insert 14 on distal portion 30 of inner cannula 12, are disposed within distal portion 20 of outer cannula 10. While stylet 16 is illustrated in the drawings as being oriented relative to inner cannula 12 such that the planes of the distal ends thereof are at an angle to one another, the orientation illustrated is primarily for clarity in the drawings and, in connection with use of the needle, the orientation of stylet 16 prior to use of the needle can be changed so that the distal ends of the stylet and inner cannula are coplanar, thus to minimize irritation and discomfort to a patient upon insertion of the needle into the patient's body. In either event, prior to use of the needle and during initial insertion thereof into a patient's body, insert 14 is advantageously enclosed within the distal portion of outer cannula 10 so as to protect the insert from infectious micro-organisms and minimize exposure of the insert to body fluids upon insertion of the needle.

In use, with the inner cannula and stylet in the retracted positions thereof, the needle is inserted into the body of a patient until the distal ends of the component parts of the needle are adjacent a lesion 70 from which a biopsy specimen is to be taken, as shown in FIG. 5. When so positioned, stylet 16 is displaced axially outwardly relative to outer cannula 10 and inner cannula 12 from its retracted position to its extended position in which specimen cutting recess 66 is located at the biopsy site in lesion 70 as shown in FIG. 7. Stylet 16 is then rotated about axis A as indicated by arrow 72 in FIG. 7 to sever a tissue specimen at the biopsy site, and inner cannula 12 is then displaced axially outwardly relative to outer cannula 10 and stylet 16 from its retracted position to its extended position shown in FIG. 8. During such movement of inner cannula 12, cutting edge 46 at the distal end thereof and arcuate wall 38 cut the tissue at the biopsy site into tissue cutting recess 66 of stylet 16 and, in passing axially across the latter recess, arcuate wall 38 radially captures the specimen therein. Simultaneous with the foregoing cutting of the specimen into recess 66, hemostatic insert 14 is pushed axially into the biopsy site by axially inner end edge 44 of the insert recess which engages against the axially inner end 52 of insert 14. During such displacement of hemostatic insert 14 into the biopsy site, the insert is radially supported by portion 67 of the stylet and by the engagement of side edges 48 and 50 of the insert with side edges 40 and 42 of the recess in distal portion 30 of the inner cannula. Further, in moving into the biopsy site with distal portion 30 of inner cannula 12, the tissue surrounding the puncture therein formed by the stylet will surround radially outer surface 56 of the insert so as to preclude unintended radially outward displacement of the insert from its recess in the inner cannula.

When insert 14 is axially displaced into the biopsy site in the foregoing manner, the insert is exposed to body fluids and the material of the inset absorbs body fluid and quickly begins to expand or swell, thus to compress the bleeding tissue surrounding the biopsy site to minimize bleeding therefrom. Such initial expansion of the insert is schematically represented by broken line 74 in FIG. 8. When the tissue specimen has been captured in recess 66 as described above, stylet 16 and inner cannula 12 are together withdrawn from the lesion to their retracted positions relative to outer cannula 10, as shown in FIG. 9, after which the needle is withdrawn from the patient. Since hemostatic insert 14 merely rests on side edges 40 and 42 of the supporting recess therefore in distal portion 30 of inner stylet 12, the insert slides therefrom and remains in the biopsy site, as also illustrated in FIG. 9, and such retention of the hemostatic insert at the biopsy site is enhanced by the swelling of the material thereof as described.

As mentioned hereinabove, the preferred material for the hemostatic insert is collagen, and the latter is preferred because of the quickness and the extent to which the material swells upon absorbing body fluids. In this respect, the hemostatic collagen insert will progressively expand radially and circumferentially such that the opposite ends 48 and 50 thereof become circumferentially constricted to form a generally circular configuration having a central opening 76 therethrough, as shown in FIG. 10 of the drawing. The material continues to swell and the ends of the insert continue to become more constricted circumferentially, and such further expansion occludes central passage 76 and compresses ends 48 and 50 against one another, as shown in FIG. 11, to produce a substantial solid plug in the biopsy site which, through such swelling and distortion from its initial configuration, prevents the flow of blood from the site. Collagen is non-bioabsorbable and, accordingly, remains in the biopsy site as opposed to dissolving in the manner of a bioabsorbable gelatin.

While considerable emphasis has been placed herein on the preferred embodiment, it will be appreciated that other embodiments can be made and that many changes can be made in the preferred embodiment without departing from the principles of the present invention. In this respect, for example, the hemostatic insert can have a circumferential contour and dimension other than the preferred contour and semi-circular dimension relative to the diameter of the inner cannula. The latter is preferred to optimize displacement of the insert from the distal portion of the inner cannula following the extraction of a biopsy specimen and to optimize the cross-sectional area of the insert upon swelling thereof and thus the insert's ability to occlude the flow of blood from the biopsy site. Further, it will be appreciated that the insert supporting recess in the distal portion of the inner cannula could be defined by a radially and axially extending recess in the outer surface of the inner cannula which does not extend completely through the wall thereof as in the preferred embodiment. Again, the latter is preferred to optimize the radial thickness of the material of the insert and thus the cross-sectional area of the hemostatic insert in the biopsy site upon absorption of body fluids by the insert. Still further, while the outer and inner cannulas and the stylet are illustrated and described herein as being provided with handles for manual manipulation of the component parts relative to one another, it will be appreciated that the needle is operable in the manner of a standard side cut needle whereby these component parts of the needle are adaptable to automated operation of the needle through the use of a "gun" for this purpose. These and other modifications of the preferred embodiment, as well as other embodiments of the present invention, will be obvious to those skilled in the art from the disclosure of the preferred embodiment herein, whereby it is to be distinctly understood that the foregoing descriptive matter is to be interpreted merely as illustrative of the present invention and not as a limitation.

Having thus described the invention it is claimed:

1. A biopsy needle for taking a biopsy specimen from a site in a patient comprising an outer tubular cannula having an axis, an inner tubular cannula coaxial with and relatively displaceably received in said outer cannula, a stylet coaxial with and relatively displaceably received in said inner cannula, each said outer and inner cannula and said stylet having a distal portion including a distal end and a proximal portion extending from said distal portion, each said inner cannula and said stylet being axially displaceable relative to said outer cannula between retracted and extended positions in which the distal portions thereof are retracted within the distal portion of said outer cannula in said retracted position and extended axially outwardly spaced from the distal end of said outer cannula to extend into said site in said extended position, said distal portion of said stylet including a cutting recess for severing said specimen at said site, said distal portion of said inner cannula including means for capturing said specimen in said cutting recess, a hemostatic insert supported on said distal portion of said inner cannula for displacement therewith from said retracted to said extended position thereof, said insert being separable from said distal portion of said inner cannula to remain at said site upon removal of said distal portions of said inner cannula and stylet therefrom, and said insert having a radially outer surface means for receiving said insert in said distal portion of said outer cannula in said retracted position of said inner cannula.

2. A needle according to claim 1, wherein the material of said insert is collagen.

3. A needle according to claim 1, wherein the material of said insert includes thrombin.

4. A needle according to claim 1, wherein said insert arcuate in cross-section relative to said axis.

5. A needle according to claim 1, wherein said distal portion of said inner cannula includes support means for said insert, said support means including pushing means engaging said insert to displace said insert into said site with said distal portion of said inner cannula during displacement of said inner cannula from said retracted to said extended position thereof.

6. A needle according to claim 5, wherein said distal portion of said inner cannula has an outer surface and said support means includes a recess extending radially inwardly of said outer surface and axially inwardly of said distal portion of said inner cannula from said distal end thereof.

7. A needle according to claim 6, wherein said recess in said distal portion of said inner cannula has an axially inner end providing said pushing means and axially extending surface means between said inner end and said distal end of said inner cannula, said insert including axially extending surface means engaging with said surface means of said recess for radially supporting said insert on said distal portion of said inner cannula.

8. A needle according to claim 7, wherein said insert is arcuate in cross-section transverse to said axis and has opposite side edges providing said axially extending surface means of said insert.

9. A needle according to claim 8, wherein said axially extending surface means of said recess in said distal portion of said inner cannula includes a pair of circumferentially spaced surfaces in a radially extending plane transverse to said axis.

10. A needle according to claim 8, wherein the material of said insert is collagen.

11. A needle according to claim 1, wherein said distal portion of said inner cannula includes an arcuate wall having circumferentially spaced apart axially extending side edges, said side edges having axially inner and outer ends, and an insert recess having a circumferentially extending inner end edge between said inner ends of said side edges and axially extending insert recess edges provided by said side edges of said arcuate wall, said insert resting on said insert recess edges between said inner and outer ends thereof, and said wall providing said means for capturing said specimen in said cutting recess.

12. A needle according to claim 11, wherein the material of said insert is collagen.

13. A needle according to claim 11, wherein said insert is arcuate transverse to said axis and has circumferentially spaced apart axially extending side edges resting on said insert recess edges.

14. A needle according to claim 11, wherein said insert recess edges lie in a radially extending plane transverse to said axis.

15. A needle according to claim 11, wherein said arcuate wall has an axially outer end edge between and lying in an inclined plane though said outer ends of said side edges of said wall.

16. A needle according to claim 15, wherein said insert has an axially outer end coplanar with said outer end edge of said wall in said inclined plane.

17. A needle according to claim 16, wherein said insert is arcuate transverse to said axis and has circumferentially spaced apart axially extending side edges resting on said insert recess edges.

18. A needle according to claim 17, wherein said insert has an axially inner end engaging said inner end edge of said insert recess.

19. A needle according to claim 18, wherein said insert recess edges lie in a radially extending plane transverse to said axis.

20. A needle according to claim 19, wherein the material of said insert is collagen.

21. A needle according to claim 11, wherein said arcuate wall has a radially outer surface and said insert is arcuate in a plane transverse to said axis and has a radially outer surface and circumferentially spaced apart axially extending side edges resting on said insert recess edges, said outer surfaces of said wall and said insert having the same radius of curvature relative to said axis.

22. A needle according to claim 21, wherein said arcuate wall has an axially outer end edge between and lying in an inclined plane though said outer ends of said side edges of said wall, and wherein said insert has an axially outer end coplanar with said outer end edge of said wall in said inclined plane.

23. A needle according to claim 22, wherein said insert recess edges lie in a radially extending plane transverse to said axis.

24. A needle according to claim 23, wherein said insert has an axially inner end engaging said inner end edge of said insert recess.

25. A needle according to claim 24, wherein the material of said insert is collagen.

26. A biopsy needle for taking a biopsy specimen from a site in a patient including an outer tubular cannula having an axis, an inner tubular cannula coaxial with and relatively displaceably received in said outer cannula, a stylet coaxial with and relatively displaceably received in said inner cannula, each said outer and inner cannula and said stylet having a distal portion including a distal end and a proximal portion extending from said distal portion, each said inner cannula and said stylet being axially displaceable relative to said outer cannula between retracted and extended positions in which the distal portions thereof are retracted within the distal portion of said outer cannula in said retracted position and extended axially outwardly spaced from the distal end of said outer cannula to extend into said site in said extended position, means for severing said specimens at said site including means for capturing said specimen in said needle, the improvement comprising a hemostatic insert supported on said distal portion of said inner cannula for displacement therewith from said retracted position to said extended position, said insert being separable from said distal portion of said inner cannula to remain at said site upon removal of said distal portion of said inner cannula from said site, and recessed surface means for receiving said insert in said distal portion of said outer cannula when said inner cannula is in said retracted position.

27. A needle according to claim 26 wherein said means for receiving said insert in said distal portion of said outer cannular includes said insert having a radially outer surface.

28. A biopsy needle for taking a biopsy specimen from a site in a patient including an outer tubular cannula having an axis, an inner tubular cannula coaxial with and relatively displaceably received in said outer cannula, a stylet coaxial with and relatively displaceably received in said inner cannula, each said outer and inner cannula and said stylet having a distal portion including a distal end and a proximal portion extending from said distal portion, each said inner cannula and said stylet being axially displaceable relative to said outer cannula between retracted and extended positions, means for severing said specimens at said site including means for capturing said specimen in said needle, the improvement comprising a hemostatic insert supported on said distal portion of said inner cannula for displacement therewith from said retracted position to said extended position, said insert being separable from said distal portion of said inner cannula to remain at said site upon removal of said distal portion of said inner cannula from said site, and means for receiving said insert in said distal portion of said outer cannula in said retracted position of said inner cannula, said distal portion of said inner cannula including support means for said insert, said support means including pushing means engaging said insert to displace said insert into said site with said distal portion of said inner cannula during displacement of said inner cannula from said retracted to said extended position.

29. A needle according to claim 26, wherein said hemostatic insert comprises collagen.

30. A needle according to claim 26, wherein said hemostatic insert includes thrombin.

31. A biopsy needle for taking a biopsy specimen from a site in a patient comprising an outer tubular cannula having an axis, an inner tubular cannula coaxial with and relatively displaceably received in said outer cannula, a stylet coaxial with and relatively displaceably received in said inner cannula, each said outer and inner cannula and said stylet having a distal portion including a distal end and a proximal portion extending from said distal portion, each said inner cannula and said stylet being axially displaceable relative to said outer cannula between retracted and extended positions in which the distal portions thereof are retracted within the distal portion of said outer cannula in said retracted position and extended axially outwardly spaced from the distal end of said outer cannula to extend into said site in said extended position, said distal portion of said stylet including a cutting recess for severing said specimen at said site, said distal portion of said inner cannula including means for capturing said specimen in said cutting recess, a hemostatic insert supported on said distal portion of said inner cannula for displacement therewith from said retracted to said extended position, said insert being separable from said inner cannula to remain at said site upon removal of said distal portion of said inner cannula therefrom, said insert having an outer surface including recessed surface means for receiving said insert within said distal portion of said outer cannula when said inner cannula is in said retracted position.

* * * * *